(12) United States Patent
Hung et al.

(10) Patent No.: US 10,117,835 B2
(45) Date of Patent: Nov. 6, 2018

(54) NOZZLE, APPARATUS, AND METHOD FOR PRODUCING MICROPARTICLES

(71) Applicant: METAL INDUSTRIES RESEARCH & DEVELOPMENT CENTRE, Kaohsiung (TW)

(72) Inventors: Cheng-Han Hung, Kaohsiung (TW);
Zong-Hsin Liu, Kaohsiung (TW);
Ying-Chieh Lin, Kaohsiung (TW);
Ming-Fang Tsai, Kaohsiung (TW);
Hai-Ching Tsou, Kaohsiung (TW);
Ying-Cheng Lu, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 27 days.

(21) Appl. No.: 15/378,292

(22) Filed: Dec. 14, 2016

(65) Prior Publication Data

US 2018/0110736 A1    Apr. 26, 2018

(30) Foreign Application Priority Data

Oct. 25, 2016  (TW) .............................. 105134449 A (51) Int. Cl.
*A61K 9/16*  (2006.01)
*B01J 2/06*  (2006.01)
(Continued)

(52) U.S. Cl.
CPC .............. *A61K 9/1682* (2013.01); *B01J 2/06* (2013.01); *B01J 2/18* (2013.01); *B01J 13/02* (2013.01);
(Continued)

(58) Field of Classification Search
None
See application file for complete search history.

(56) References Cited

U.S. PATENT DOCUMENTS 1,637,377 A * 8/1927 Heicke ...................... B22F 9/08
                                                              264/DIG. 37
3,123,855 A * 3/1964 Fischer ...................... B01J 2/06
                                                              425/6
(Continued)

FOREIGN PATENT DOCUMENTS

CN         205235997 U     5/2016
JP         S4868474 A      9/1973
(Continued)

*Primary Examiner* — Mary Lynn F Theisen
(74) *Attorney, Agent, or Firm* — Alan D. Kamrath; Kamrath IP Lawfirm, P.A.

(57) ABSTRACT

A nozzle includes a nozzle body having a fluid passageway to which extension tubes are communicated. Each extension tube includes an end having an outlet port. The outlet ports are spaced from each other. An apparatus includes the nozzle, a fluid tank into which the extension tubes extends, a fluid shear device mounted in the fluid tank, and a temperature control system in which the fluid tank is mounted. A method includes filling a water phase fluid into the fluid tank. An oil phase fluid flows out of the nozzle body via the outlet ports. The water phase fluid is disturbed and flows out of the outlet ports to form semi-products of microparticles in the fluid tank. Each semi-product has an inner layer formed by the oil phase fluid and an outer layer formed by the water phase fluid. The outer layers of the semi-products are removed to form microparticles.

18 Claims, 11 Drawing Sheets

(51) Int. Cl.
  *B01J 2/18* (2006.01)
  *B01J 13/02* (2006.01)
  *B01J 13/08* (2006.01)
  *B01J 13/12* (2006.01)
  *B01J 13/20* (2006.01)
  *B29B 9/12* (2006.01)
  *B29B 9/16* (2006.01)
  *B29B 9/10* (2006.01)
  *B29K 105/00* (2006.01)

(52) U.S. Cl.
  CPC ............... *B01J 13/08* (2013.01); *B01J 13/12* (2013.01); *B01J 13/20* (2013.01); *B29B 9/10* (2013.01); *B29B 9/12* (2013.01); *B29B 9/16* (2013.01); *A61K 9/1647* (2013.01); *B29B 2009/168* (2013.01); *B29K 2105/0035* (2013.01); *B29K 2995/006* (2013.01)

(56) References Cited

U.S. PATENT DOCUMENTS

| | | | |
|---|---|---|---|
| 3,933,955 A * | 1/1976 | Lysher | B01J 2/08 264/13 |
| 5,492,701 A | 2/1996 | Cervos et al. | |
| 5,882,680 A * | 3/1999 | Suzuki | A61K 9/4833 424/451 |
| 6,998,074 B1 * | 2/2006 | Radulescu | A61K 9/1682 264/14 |
| 2007/0056637 A1 * | 3/2007 | Okubo | B01J 2/06 137/551 |
| 2010/0237523 A1 * | 9/2010 | Bohmer | A61K 9/1647 264/13 |
| 2017/0101514 A1 * | 4/2017 | Ishihara | C08J 3/16 |

FOREIGN PATENT DOCUMENTS

| | | |
|---|---|---|
| JP | S5335673 A | 4/1978 |
| JP | S58210072 A | 12/1983 |
| JP | S61137836 A | 6/1986 |
| JP | H05177157 A | 7/1993 |
| JP | H0751343 A | 2/1995 |
| JP | 2003311944 A | 11/2003 |
| JP | 2012250476 A | 12/2012 |
| WO | WO2012100205 A2 | 7/2012 |

* cited by examiner

NOZZLE, APPARATUS, AND METHOD FOR PRODUCING MICROPARTICLES

CROSS REFERENCE TO RELATED APPLICATIONS

The application claims the benefit of Taiwan application serial No. 105134449, filed on Oct. 25, 2016, and the subject matter of which is incorporated herein by reference.

BACKGROUND

1. Technical Field

The present disclosure relates to a nozzle, an apparatus, and a method for producing microparticles and, more particularly, to a nozzle, an apparatus, and a method for mass production of microparticles.

2. Description of the Related Art

Microparticles, also known as microspheres, are spherical particles having a diameter smaller than 1000 μm, are generally used as microcarriers for releasing drug, and have become one of the emerging drug delivery technologies due to the characteristics of targeting, controlled release, stability, and surface modifiability.

Since the diameters of microparticles are small and the demanded quantity is so huge, the important aim of the microparticle formation technology is mass production of microparticles. For example, a conventional nozzle 9 shown in FIG. 1 can be used for mass production of microparticles.

Figure 1:
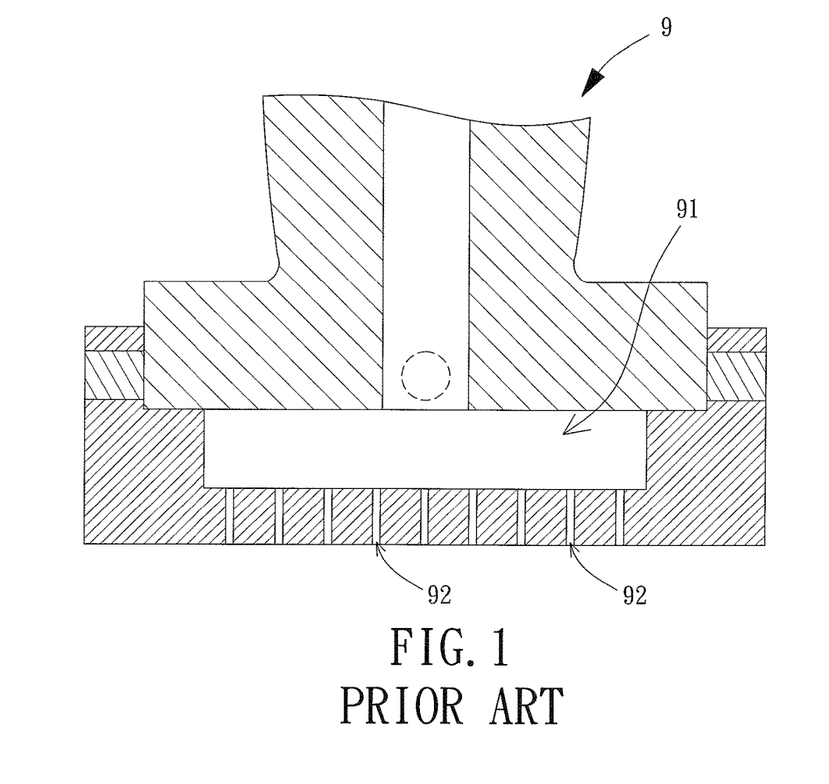
FIG. 1 is a diagrammatic view of a conventional nozzle for producing microparticles.

Specifically, the conventional nozzle 9 for producing microparticles includes a fluid passageway 91 and a plurality of openings 92 intercommunicated with the fluid passageway 91. An oil phase solution can be filled into the fluid passageway 91. The oil phase solution flows out of the nozzle 9 via the openings 92 and forms a droplet on each opening 92 by surface tension. When the weight of each droplet is large enough to overcome the surface tension, the droplet exits the corresponding opening 92 and falls into a water phase solution which envelops the droplet formed by the oil phase solution, assisting in curing and shaping of the droplet. Mass production of microparticles is, thus, achieved.

Although the above conventional nozzle 9 can proceed with mass production of microparticles, the surface extensions or pressures in the openings 92 could be different, leading to diverse microparticle diameters. Thus, the microparticles have poor uniformity and, thus, have different drug releasing effects.

Furthermore, the diameters of the microparticles are influenced by the concentration of the oil phase solution, leading to difficulties in control of the diameters of the microparticles while using the conventional nozzle 9 to produce microparticles. Furthermore, if the concentration of the oil phase solution filled into the fluid passageway 91 is too high (e.g., the concentration of the polymer material is larger than 9 wt %), each droplet must be accumulated to be heavier for exiting the corresponding opening 92, resulting in an oversize microparticle that might not fulfill the production demand of microparticles. As a result, the conventional nozzle 9 cannot be used to produce microparticles from a high-concentration oil phase solution. Accordingly, it is difficult to control the diameters of the microparticles produced by the conventional nozzle 9, and the conventional nozzle 9 has fewer applications.

Furthermore, it takes a long period of time for the oil phase solution to accumulate on each opening 92 to form a droplet until the weight of the droplet is sufficient to exit the opening 92, such that the productivity of microparticles produced by the conventional nozzle 9 is low. Furthermore, since the water phase solution is a static fluid, the droplets falling into the water phase solution are apt to aggregate, such that the respective droplet cannot be enveloped and shaped by the water phase solution, resulting in a low yield of microparticles produced by the conventional nozzle 9.

Thus, improvement to the conventional nozzle 9 and the conventional method for producing microparticles is necessary.

SUMMARY

To solve the above problems, the present disclosure provides a nozzle, an apparatus, and a method for producing microparticles of a uniform size.

A nozzle for producing microparticles according to the present disclosure includes a nozzle body having a fluid passageway therein. A plurality of extension tubes is communicated with an end of the fluid passageway. Each of the plurality of extension tubes includes a distant end having an outlet port and located distant to the fluid passageway. The outlet ports of the plurality of extension tubes are spaced from each other.

In an example, the plurality of extension tubes is parallel to each other, such that an oil phase fluid can flow out of the nozzle body in the same direction.

In an example, the outlet port of each of the plurality of extension tubes has a diameter, and each of the plurality of extension tubes includes a tubular wall having a thickness smaller than the diameter. Thus, the surface area of each of the plurality of extension tubes at an outer periphery of the outlet port is reduced to make an oil phase fluid difficult to accumulate in each outlet port, thereby reducing adverse influence on the diameters of the microparticle products by the surface tension.

In an example, the outlet port of each of the plurality of extension tubes has a diameter. Two adjacent extension tubes have a minimum spacing therebetween. The minimum spacing is larger than the diameter to avoid mixing of the continuous oil phase fluids flowing out of adjacent extension tubes.

In an example, the distant end of each of the plurality of extension tubes having the outlet port is an inclined end. Thus, when the oil phase fluid flows out of each outlet port, the contact area between the oil phase fluid and each of the plurality of extension tubes can be further reduced to reliably avoid the oil phase fluid from accumulating in each outlet port, thereby more effectively reducing the adverse influence on the diameters of the microparticle products by the surface tension.

In an example, the distant end of each of the plurality of extension tubes having the outlet port includes a layer of hydrophobic material. Thus, when the oil phase fluid flowing out of each outlet port comes in contact with the layer of hydrophobic material, the oil phase fluid is less likely to adhere to each of the plurality of extension tubes to reliably prevent the oil phase fluid from accumulating in each outlet port, thereby more effectively reducing the influence on the diameters of the microparticle products by the surface tension.

An apparatus for producing microparticles according to the present disclosure includes the above-mentioned nozzle. The apparatus further includes a fluid tank into which the plurality of extension tubes of the nozzle body extends, a fluid shear device mounted in the fluid tank, and a temperature control system in which the fluid tank is mounted.

In an example, a water phase fluid is received in the fluid tank and has a level that defines a liquid level, and the outlet port of each of the plurality of extension tubes is located under the liquid level, such that each outlet port is located in the water phase fluid.

In an example, the apparatus further includes a collection tank. An inlet pipe and an outlet pipe are coupled to the fluid tank and extend through an outer wall of the fluid tank. The collection tank is intercommunicated with the outlet pipe. Thus, the water phase fluid and the semi-products of microparticles in the fluid tank flow through the outlet ports into the collection tank. A worker can collect the semi-products of microparticles by using the collection tank. The water phase fluid can be filled through the inlet pipe to maintain the liquid level of the water phase fluid, thereby assuring the outlet port of each extension tube is located in the water phase fluid.

In an example, the fluid shear device includes a stirring device mounted in the fluid tank. The stirring device drives the water phase fluid to flow, thereby using the shear force of the flowing water phase fluid to interrupt the oil phase fluid flowing out of the nozzle body.

In another example, the fluid shear device includes a supersonic wave generator mounted to an outer wall of the fluid tank. The supersonic wave generator makes the water phase fluid vibrate to interrupt the continuous oil phase fluids flowing out of the nozzle body.

A method for producing microparticles according to the present disclosure can be carried out by the above apparatus for forming microparticles and includes filling a water phase fluid into the fluid tank, with the outlet port of each of the plurality of extension tubes located in the water phase fluid; filling an oil phase fluid into the fluid passageway of the nozzle body, and making the oil phase fluid flow out of the nozzle body via the outlet ports of the plurality of extension tubes; activating the fluid shear device to disturb the water phase fluid (such as activating the stirring device to drive the water phase fluid to flow or activating the supersonic wave generator to vibrate the water phase fluid), and making the oil phase fluid flowing out of the outlet ports of the plurality of extension tubes form a plurality of semi-products of microparticles in the fluid tank; collecting the semi-products of microparticles, with each of the plurality of semi-products of microparticles including an inner layer formed by the oil phase fluid and an outer layer formed by the water phase fluid; and removing the outer layers of the plurality of semi-products of microparticles.

In an example, the oil phase fluid is produced by heating a polymer to a glass transition temperature, such that the oil phase fluid can flow into the fluid passageway of the nozzle body.

In an example, the temperature control system is activated to maintain the water phase fluid at a predetermined temperature before the oil phase fluid enters the fluid passageway, and the predetermined temperature is equal to or lower than the glass transition temperature of the oil phase fluid. Thus, when the oil phase fluid forms the microdroplets, the temperature of the water phase fluid can assist in curing and shaping of the microdroplets.

In another example, the oil phase fluid is produced by adding an organic solvent into a polymer, such that the oil phase fluid can flow into the fluid passageway of the nozzle body.

In an example, the oil phase fluid is a biodegradable polymer mixed with a pharmaceutically active ingredient. Thus, when the microparticle products are given to an organism, a slow releasing effect of the pharmaceutically active ingredient is achieved by enveloping of the biodegradable polymer.

In another example, the oil phase fluid is a biodegradable polymer mixed with a gas. Thus, the microparticle product can contain a plurality of micro gas bubbles to increase the drug releasing effect.

In an example, when the oil phase fluid enters the fluid passageway, the fluid passageway is pressurized to drive the oil phase fluid into the water phase fluid via each outlet port, thereby generating a continuous oil phase fluid. Thus, the shear force or vibration of the water phase fluid is used to interrupt the continuous oil phase fluids to thereby form microdroplets, and the water phase fluid envelops the outer layer of each microdroplet, thereby forming the semi-products of microparticles.

In an example, the water phase fluid is a 1-15% polyvinyl alcohol solution. Thus, the plurality of semi-products of microparticles can be processed by drying or can be washed by an aqueous solution to remove the outer layers of the plurality of semi-products, and the inner layers of the plurality of semi-products form microparticle products.

By the nozzle, apparatus, and method for producing microparticles according to the present disclosure, the nozzle body includes a plurality of extension tubes, such that the produced microparticle products have diameters that are more uniform, increasing the uniformity of microparticles. Furthermore, by adjusting the stirring device or the supersonic wave generator, the diameters of the formed microparticles can be controlled more precisely. Furthermore, it is suitable to produce microparticles from high-concentration oil phase water. The precise control in the diameters of the microparticles is increased, and the applications of the apparatus and method for producing microparticles are broadened. Furthermore, the oil phase fluid can continuously flow out of the nozzle body at a faster speed to reduce the production time of the method for producing microparticles, increasing the productivity of microparticles. Furthermore, the flow and vibrational energy of the water phase fluid can assure each microdroplet is enveloped and shaped by the water phase fluid, increasing the yield of the microparticles.

The present disclosure will become clearer in light of the following detailed description of illustrative embodiments of the present disclosure described in connection with the drawings.

DETAILED DESCRIPTION

Figure 2:
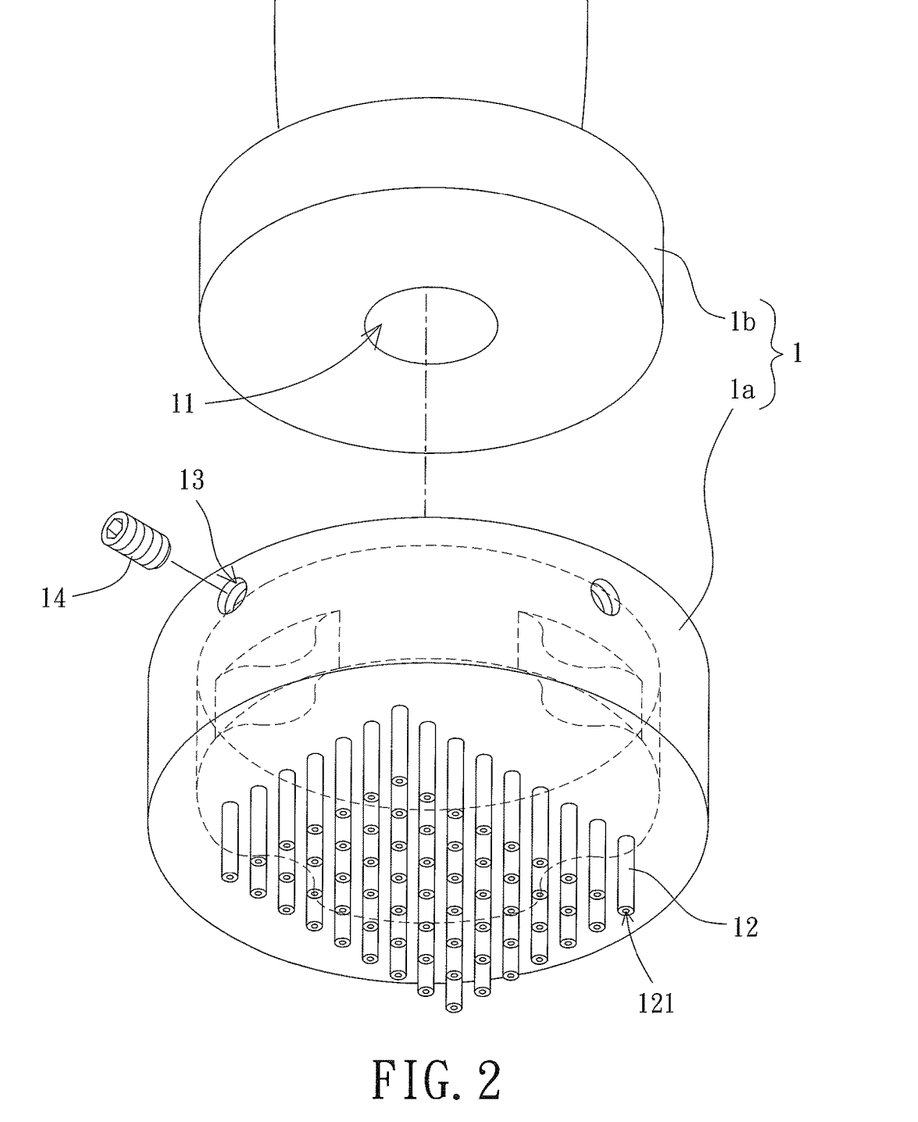
FIG. 2 is an exploded, perspective view of a nozzle for producing microparticles of an embodiment according to the present disclosure.
Figure 3:
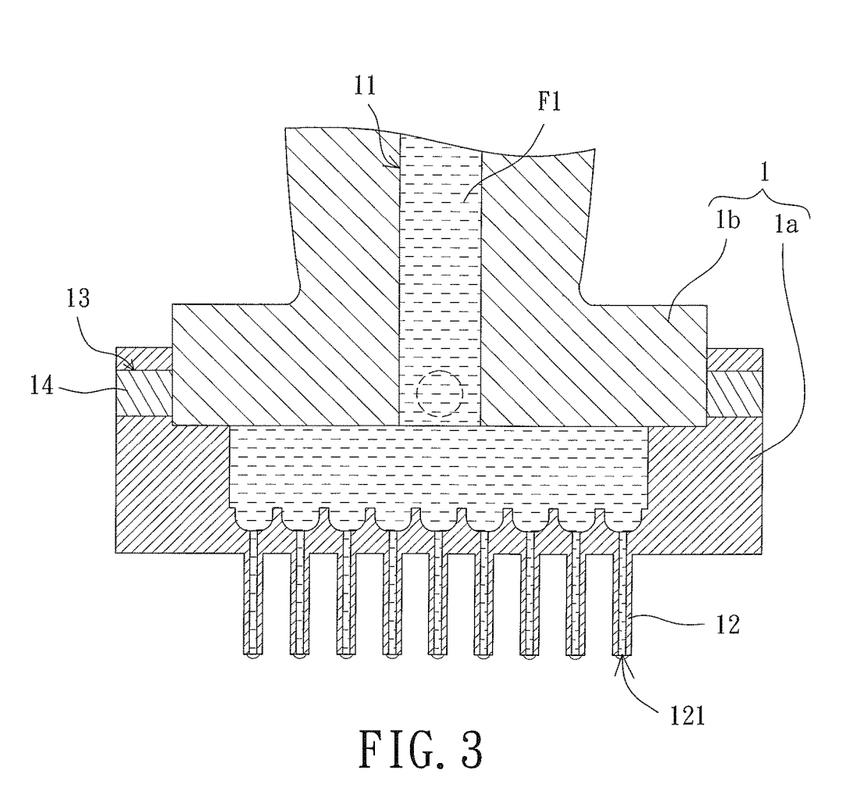
FIG. 3 is a cross sectional view of the nozzle of FIG. 2.

With reference to FIGS. 2 and 3, a nozzle for producing microparticles according to the present disclosure includes a nozzle body 1 having a fluid passageway 11 therein. A plurality of extension tubes 12 is communicated with an end of the fluid passageway 11. Each extension tube 12 includes a distant end having an outlet port 121 and located distant to the fluid passageway 11. The outlet ports 121 of the extension tubes 12 are spaced from each other. The extension tubes 12 can be parallel to each other. Preferably, the outlet ports 121 of the extension tubes 12 are on the same plane.

An oil phase fluid F1 can be filled into the fluid passageway 11, can flow along the fluid passageway 11, and can flow out of the nozzle body 1 via the outlet ports 121 of the extension tubes 12. Although the oil phase fluid F1 will still withstand surface tension at each outlet port 121, and since the surface area around an outer periphery of the outlet port 121 of each extension tube 12 is insufficient for the oil phase fluid F1 to adhere, the oil phase fluid F1 is difficult to accumulate on each outlet port 121.

Figure 4:
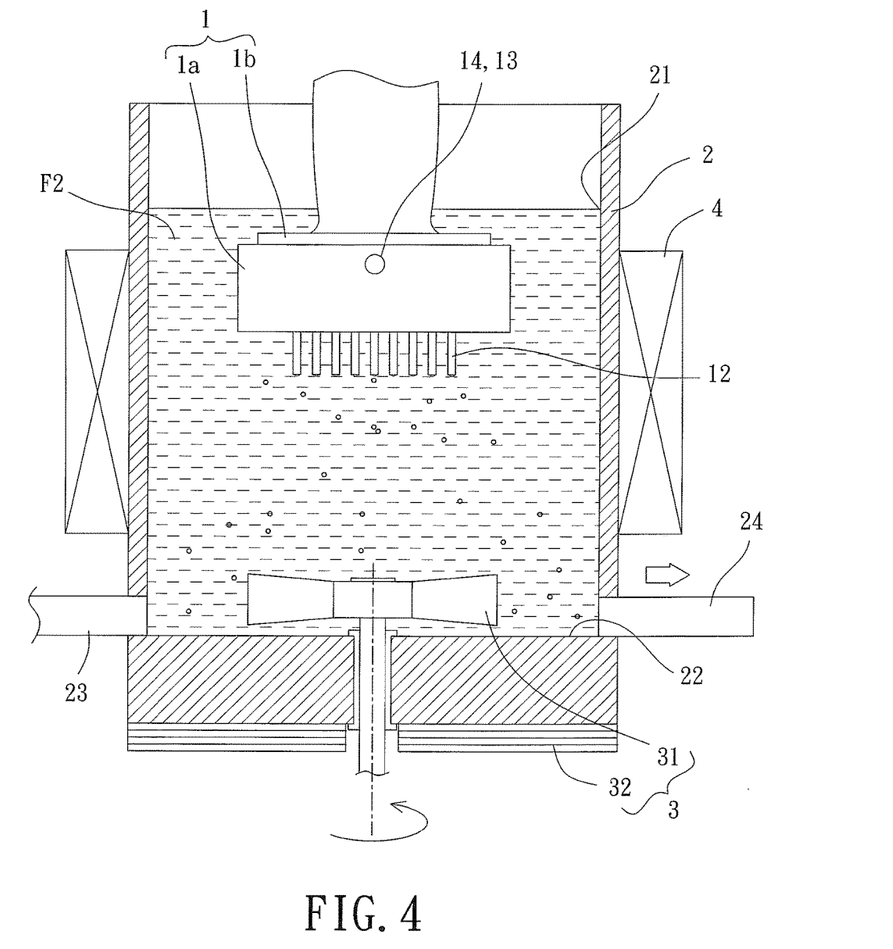
FIG. 4 is a cross sectional view of an apparatus for producing microparticles of an embodiment according to the present disclosure.

With reference to FIG. 4, in practical use of an embodiment according to the present disclosure, the nozzle for producing microparticles can be used in an apparatus for producing microparticles including a fluid tank 2, a fluid shear device 3, and a temperature control system 4. The extension tubes 12 of the nozzle body 1 extend into the fluid tank 2. The fluid shear device 3 is mounted to the fluid tank 2. The fluid shear device 3 can include a stirring device 31 or a supersonic wave generator 32 or both. In this embodiment, the fluid shear device 3 includes both of the stirring device 31 and the supersonic wave generator 32. The stirring device 31 is mounted in the fluid tank 2. The supersonic wave generator 32 is mounted to an outer wall of the fluid tank 2. The fluid tank 2 is mounted in the temperature control system 4.

Specifically, the fluid tank 2 can receive a water phase fluid F2. The water phase fluid F2 received in the fluid tank 2 includes a level defining a liquid level 21. The extension tubes 12 of the nozzle body 1 extends into the fluid tank 2, such that the outlet port 121 of each extension tube 12 is located under the liquid level 21 and a bottom 22 of the fluid tank 2. Namely, the outlet ports 121 are located in the water phase fluid F2. The fluid shear device 3 is used to disturb the water phase fluid F2 in the fluid tank 2. The stirring device 31 can be driven by a motor to drive the water phase fluid F2 to flow. The supersonic wave generator 32 can generate high frequency vibrations. For example, the supersonic wave generator 32 is made of piezoelectric material and can include power capable of generating high frequency electrical energy. The piezoelectric material can turn the high frequency electrical energy into high frequency vibrations which are transmitted through the outer wall of the fluid tank 2 to the water phase fluid F2, causing vibrations of the water phase fluid F2. The temperature control system 4 can control the temperature of the water phase fluid F2 to maintain the water phase fluid F2 at a predetermined temperature.

The oil phase fluid F1 is produced by heating a polymer to a glass transition temperature (Tg) or by adding a small amount of organic solvent (such as ethyl acetate, ethyl acetate, etc.) into a polymer. The polymer can be a biodegradable polymer including aliphatic polyesters, aliphatic-aromatic copolyesters, polylactide-aliphatic copolyesters, polycaprolactone, polyglutamic acid, poly-hydroxy acid ester, or polylactide. More specifically, aliphatic polyesters can be polyglycolic acid, polybutylene succinate butanediamine, or polyethylene succinate. Aliphatic-aromatic copolyesters can be polyethylene terephthalate-polyoxyethylene. Polylactide-aliphatic copolyesters can be polylactic glycolic acid. However, the present disclosure is not limited to these. Other biodegradable polymers used as drug microcarriers can be used as the polymer. In this embodiment, the polymer is preferably polycaprolactone, polylactide, or polylactic glycolic acid. Polycaprolactone has excellent biocompatibility and miscibility and has excellent molecular flowability in the organism due to a low glass transition temperature, presenting excellent permeability for active pharmaceutical ingredients having a low molecular weight.

Figure 5:
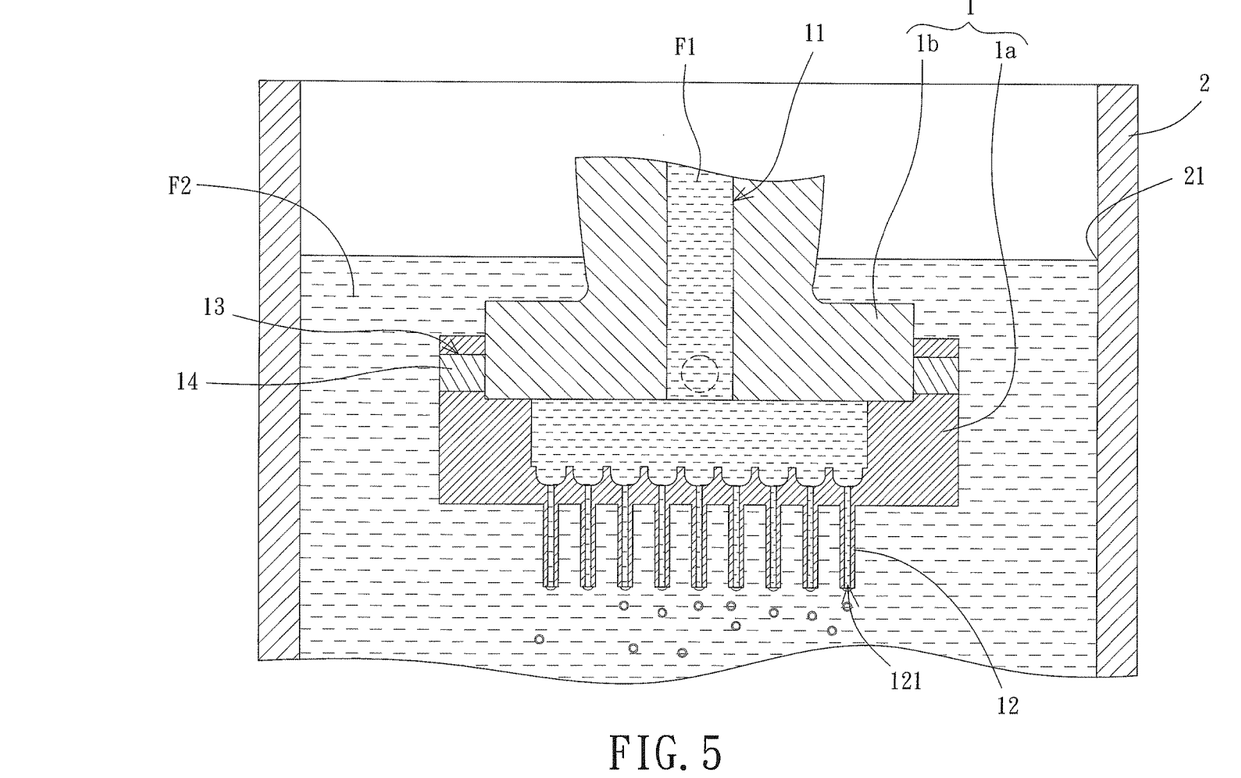
FIG. 5 is an enlarged view of a portion of the apparatus of FIG. 4.

With reference to FIGS. 4 and 5, a method for producing microparticles of an embodiment according to the present disclosure can be carried out by the apparatus for producing microparticles. The method for producing microparticles of this embodiment includes filling the water phase fluid F2 into the fluid tank F2. The temperature control system 4 is activated to maintain the water phase fluid F2 at a predetermined temperature. The predetermined temperature is equal to or lower than the glass transition temperature (Tg) of the oil phase fluid F1. In this embodiment, the water phase can be, but is not limited to, a 1-15% polyvinyl acetate (PVA) solution. The outlet port 121 of each extension tube 12 extends into the fluid tank 2. The oil phase fluid F1 is filled into the fluid passageway 11 of the nozzle body 1 and flows out of the nozzle body 1 via the outlet port 121 of each extension tube 12 to generate a continuous oil phase fluid F1. The stirring device 31 is driven to rotate, and the supersonic wave generator 32 is activated. Preferably, the fluid passageway 11 is pressurized to make the oil phase fluid F1 flow through the fluid passageway 11 at a certain speed and to continuously drive the oil phase fluid F1 into the water phase fluid F2 via each outlet port 121, thereby generating the continuous oil phase fluid F1.

Figure 6:
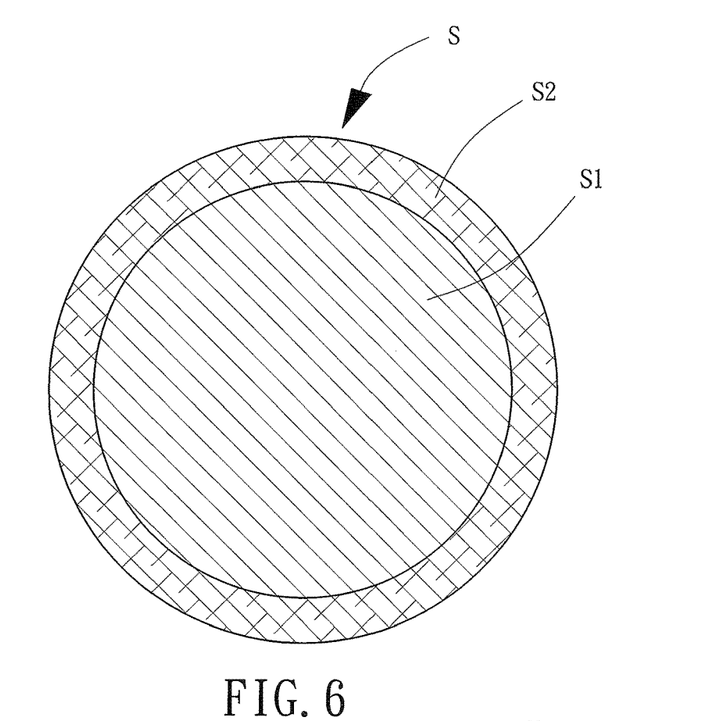
FIG. 6 is a diagrammatic view of an example of a semi-product of a microparticle produced by the apparatus of FIG. 4.

The stirring device 31 drives the water phase fluid F2 to flow, thereby using the shear force of the flowing water phase fluid F2 to interrupt the continuous oil phase fluid F1 flowing out of each outlet port 121, such that the oil phase fluid F1 forms microdroplets. Alternatively, the supersonic wave generator 32 makes the water phase fluid F2 vibrate to interrupt the continuous oil phase fluid F1 flowing out of each outlet port 121, such that the oil phase fluid F1 forms microdroplets. At this time, the water phase fluid F2 received in the fluid tank 2 envelops the outer layers of the microdroplets (namely, emulsification) to assist in curing and shaping of the microdroplets, thereby forming semi-products S of microparticles in the fluid tank 2, as shown in FIG. 6. Each semi-product S includes an inner layer S1 formed by the oil phase fluid F1 and an outer layer S2 formed by the water phase fluid F2.

Figure 7:
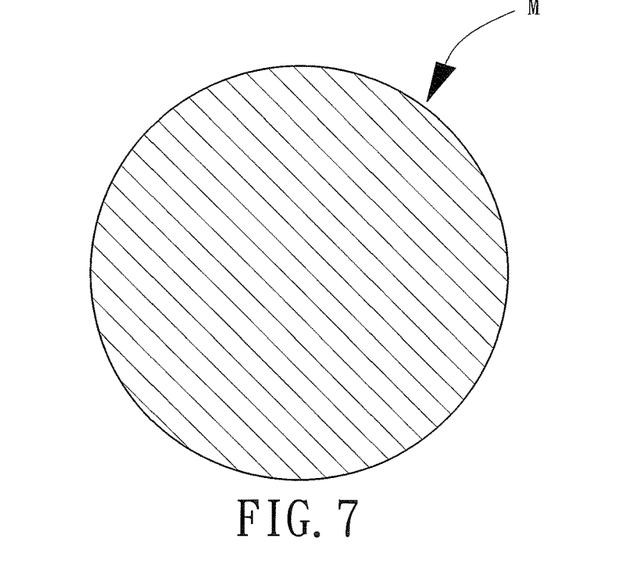
FIG. 7 is a diagrammatic view of a microparticle product of FIG. 6.
Figure 8:
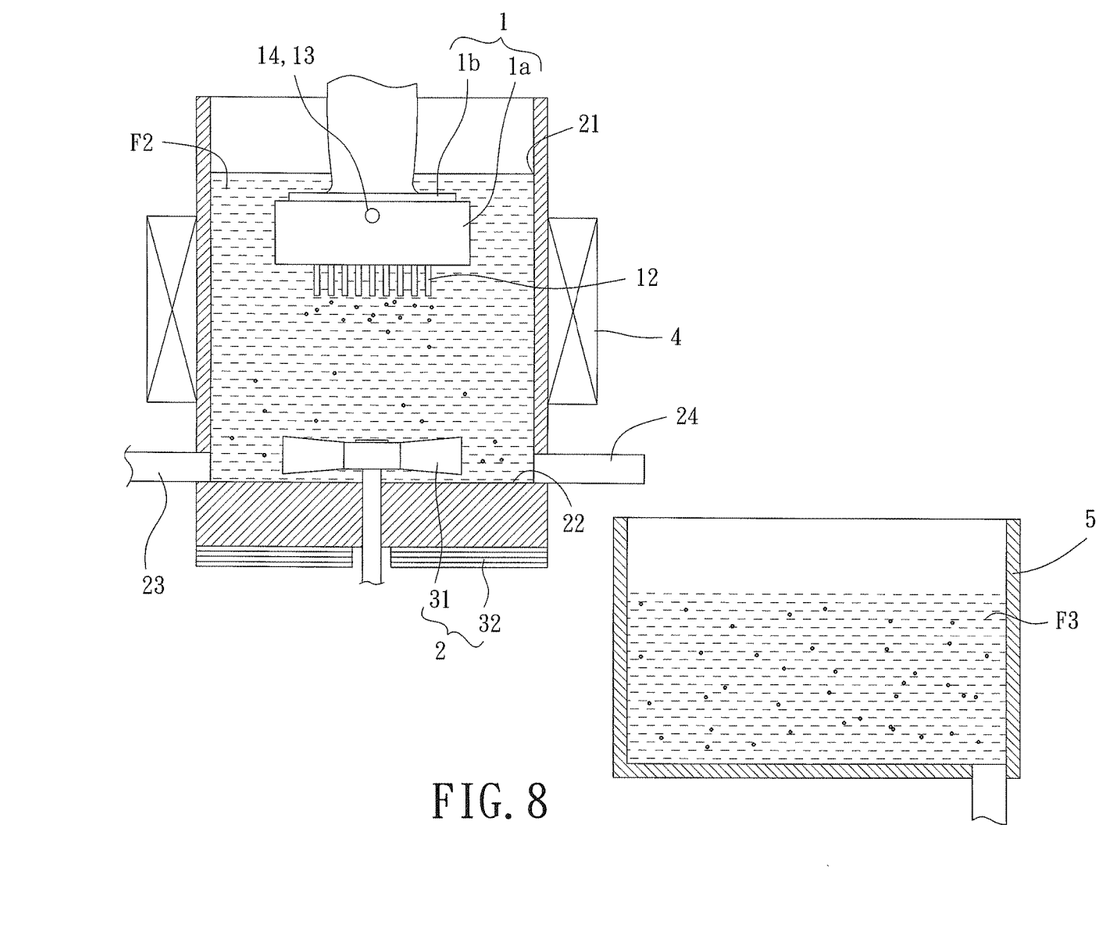
FIG. 8 is a cross sectional view of an apparatus for producing microparticles of another embodiment including a collection tank according to the present disclosure.

Then, the semi-products S are collected, and the outer layers S2 formed by the water phase fluid F2 are removed to form microparticle products M each of which is formed by the inner layer S1 formed by the oil phase fluid F1 (see FIG. 7). For example, the semi-products S are dried (such as by hot air) to evaporate the outer layers S2. Alternatively, the semi-products S are washed by an aqueous solution to remove the outer layers S2, forming microparticle products M merely formed by the oil phase fluid F1. The worker can collect the semi-products S by using the fluid tank 2. Alternatively, as shown in FIGS. 4 and 8, an inlet pipe 23 and an outlet pipe 24 are coupled to the fluid tank 2 and extend through a wall of the fluid tank 2. Preferably, the outlet pipe 24 is mounted to a position adjacent to the bottom 22. The apparatus for producing microparticles can further include a collection tank 5 intercommunicated with the outlet pipe 24 of the fluid tank 2. Thus, the water phase fluid F2 along with the semi-products S can flow through the outlet pipe 24 into the collection tank 5, and a worker can collect the semi-products S in the collection tank 5. Furthermore, the water phase fluid F2 can be filled into the inlet pipe 23 to maintain the water phase fluid F2 in the fluid tank 2 at the liquid level 21, thereby assuring that the outlet port 121 of each extension tube 12 is located in the water phase fluid F2.

The conventional nozzle 9 relies on surface tension to form microdroplets on the openings 92, leading to diverse diameters of the microparticles. By contrast, the nozzle, apparatus, and method according to the present disclosure use the nozzle body 1 to generate continuous oil phase fluid F1 and use the shear force or vibrations of the water phase fluid F2 to interrupt the continuous oil phase fluids F1, thereby forming the microparticle products M. Since the surface area around the outer periphery of the outlet port 121 of each extension tube 12 is insufficient for the oil phase fluid F1 to adhere, the oil phase fluid F1 is difficult to accumulate on each outlet port 121. As a result, the microparticle products M have more uniform diameters, increasing the uniformity of the microparticles.

Furthermore, since the apparatus and method for producing microparticles according to the present disclosure use the shear force or vibrations of the water phase fluid F2 to interrupt the continuous oil phase fluids F1, the rotational speed of the stirring device 31 can be adjusted to control the shear force of the water phase fluid F2. Alternatively, the frequency and amplitude of the supersonic wave generator 32 can be adjusted to control the vibrations of the water phase fluid F2. Thus, precise control of the diameters of the microparticle products M can be achieved. For example, when the oil phase fluid F1 flowing into the passageway 11 has a high concentration, the rotational speed of the stirring device 31 or the amplitude of the supersonic wave generator 32 can be increased to increase the shear force generated by the water phase fluid F2, assuring that the water phase fluid F2 can effectively interrupt the oil phase fluid F1, and avoiding the diameters of the microparticle products M from being adversely affected by the concentration of the oil phase fluid F1 and thereby precisely controlling the diameters of the microparticle products M. Accordingly, in comparison with the conventional nozzle 9 having difficulties in controlling the diameters of microparticles and failing to produce microparticle products from a high-concentration oil phase solution, the nozzle, apparatus, and method for producing microparticles according to the present disclosure can increase the control precision of the diameters of the microparticles and can be applied in high-concentration oil phase fluid F1 (e.g., the concentration of the polymer material is larger than 9 wt %), broadening the applications.

Furthermore, the nozzle, apparatus and method for producing microparticles according to the present disclosure make the oil phase fluid F1 flow out of the nozzle body 1 via the outlet port 121 of each extension tube 12, such that the oil phase fluid F1 is able to flow through the fluid passageway 11 and each extension tube 12 at a certain speed to produce continuous oil phase fluids F1, thereby forming the microparticle products M. In comparison with the long period of time required by the conventional nozzle 9 for forming the droplets and discharging the droplets, the nozzle, apparatus, and method for producing microparticles according to the present disclosure permit the oil phase fluid F1 to flow out of the nozzle body 1 at a faster speed to reduce the time for producing the microparticles, increasing the productivity of the microparticles.

Furthermore, by using the stirring device 31 to drive the water phase fluid F2 to flow or by using the supersonic wave generator 32 to vibrate the water phase fluid F2, the microdroplets formed by the oil phase fluid F1 are prevented from aggregating in the water phase fluid F2. Accordingly, the apparatus and method for producing microparticles according to the present disclosure can assure each microdroplet is enveloped by the water phase fluid F2, increasing the yield of microparticles.

According to the above technical concept, the features of the nozzle, apparatus, and method for producing microparticles according to the present disclosure will be described hereinafter.

Figure 9:
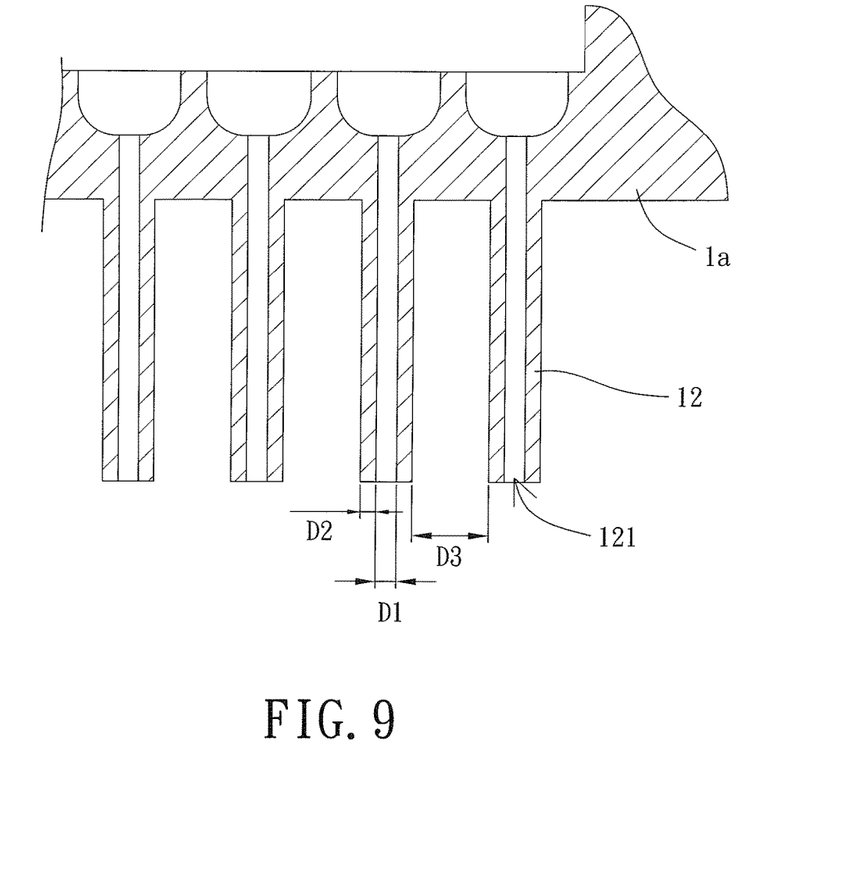
FIG. 9 is a partial, enlarged view of extension tubes of a nozzle for producing microparticles of an embodiment according to the present disclosure.

With reference to FIG. 9, the outlet port 121 of each extension tube 12 has a diameter D1. Each extension tube 12 includes a tubular wall having a thickness D2. The thickness D2 is preferably smaller than the diameter D1 to reduce the surface area of each extension tube 12 at the outer periphery of the outlet port 121. Thus, the oil phase fluid F1 is difficult to accumulate in each outlet port 121, thereby reducing adverse influence on the diameters of the microparticle products M by the surface tension.

Figure 10:
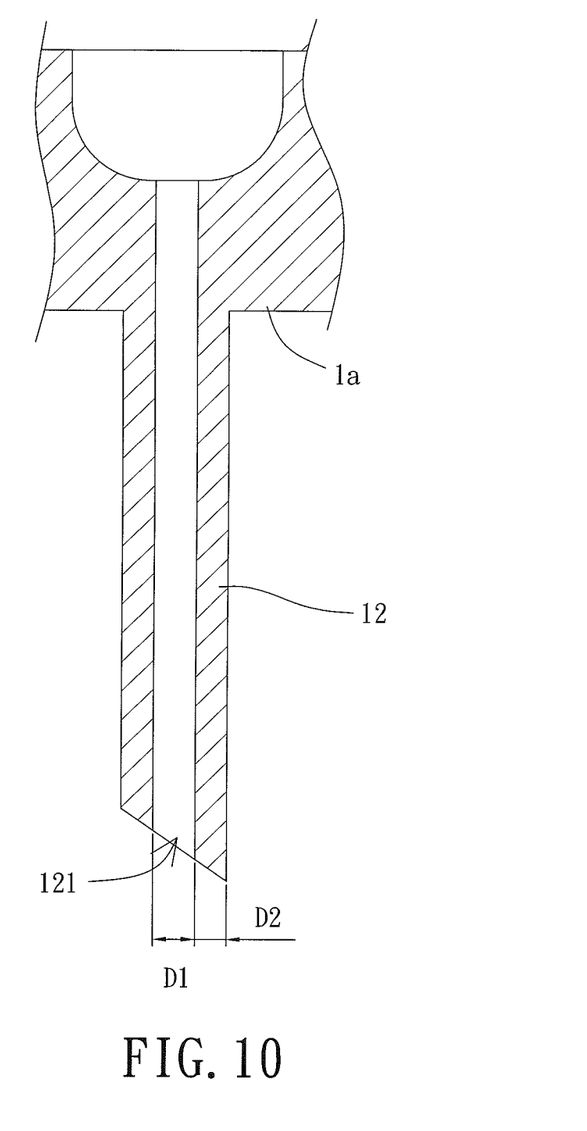
FIG. 10 is a partial, enlarged view of an extension tube of a nozzle for producing microparticles of another embodiment according to the present disclosure.

In this embodiment, the distant end of each extension tube 12 having the outlet port 121 can be a flat end. However, as shown in FIG. 10, in some embodiments of the present disclosure, the distant end of each extension tube 12 having the outlet port 121 is an inclined end. Thus, when the oil phase fluid F1 flows out of each outlet port 121, the contact area between the oil phase fluid F1 and each extension tube 12 can be further reduced to reliably avoid accumulation of the oil phase fluid F1 on each outlet port 121, thereby more effectively reducing the influence on the diameters of the microparticle products M by the surface tension.

In some embodiments according to the present disclosure, the distant end of each extension tube 12 having the outlet port 121 includes a layer of hydrophobic material. The hydrophobic material can be, but is not limited to, silicon dioxide ($SiO_2$) or titanium dioxide ($TiO_2$). The layer of hydrophobic material can be, but is not limited to, disposed on the distant end of each extension tube 12 having the outlet port 121 by plating. By providing the hydrophobic material on the outlet port 121 of each extension tube 12, the oil phase fluid F1 comes in contact with the layer of hydrophobic material when flowing out of each outlet port 121, such that the oil phase fluid F1 is difficult to adhere to each extension tube 12, reliably preventing the oil phase fluid F1 from accumulating on each outlet port 121 to more effectively reduce the adverse influence on the diameters of the microparticle products M by the surface tension.

It is noted that the diameter D1 decides the flow of the continuous oil phase fluid F1 flowing out of each outlet port 121 to thereby control the diameter of the microparticle products M. Thus, the diameter D1 corresponds to the diameter of the microparticle products M to be produced. For example, if the diameter of the microparticle products M to be produced is 100 µm, the diameter D1 can be designed to be about 100 µm. Alternatively, if the diameter of the microparticle products M to be produced is below 5 µm, the diameter D1 can be designed to be about 5 µm. More specifically, if it is desired to produce microparticle products M smaller than the diameter D1, the velocity of the oil phase fluid F1, the rotational speed of the stirring device 31, or the frequency of the supersonic wave generator 32 can be adjusted to achieve this purpose. Thus, the embodiments of the present disclosure are not limited to produce microparticle products M having diameters the same as the diameter D1 and can produce microparticle products M having a diameter smaller than the diameter D1. Accordingly, although the microparticle products M in the embodiments are of microscale, the present disclosure can make the diameters of the microparticle products M reach nanoscale.

With reference to FIGS. 2 and 3, the nozzle body 1 of the nozzle of an embodiment according to the present disclosure includes a core 1a and a seat 1b. The core 1a is detachably mounted to the seat 1b. In an example, the core 1a includes an assembly portion 13 for detachable coupling with the seat 1b. In this embodiment, the assembly portion 13 is a screw hole, and a fastener 14 extends through the assembly portion 13 to fix the core 1a to the seat 1b. The passageway 11 extends through the seat 1b. The extension tubes 12 are mounted to the core 1a. Since the nozzle for producing microparticles of an embodiment according to the present disclosure includes the core 1a detachably mounted to the seat 1b, the nozzle can be used to produce microparticle products M of a different diameter by changing a core 1a having a different diameter D1 in the outlet ports 121, thereby increasing utility of the nozzle for producing microparticles.

Furthermore, two adjacent extension tubes 12 of the nozzle body 1 have a minimum spacing D3 therebetween (see FIG. 9). The minimum spacing D3 is preferably larger than the diameter D1 to avoid mixing of continuous oil phase fluids F1 flowing out of adjacent extension tubes 12.

As mentioned above, the method for producing microparticles of an embodiment according to the present disclosure pressurizes the passageway 11 to make the oil phase fluid F1 flow through the passageway 11 at a certain speed, such that the oil phase fluid F1 is continuously driven into the water phase fluid F2 via each outlet port 121. With reference to FIG. 4, in this embodiment, the nozzle body 1 extends from a horizontal, upper position of the fluid tank 2 into the fluid tank 2 of the apparatus for producing microparticles. Alternatively, with reference to FIG. 11, in some embodiments according to the present disclosure, the nozzle body 1 extends from a horizontal, lower position of the fluid tank 2 into the fluid tank 2. Similarly, in other embodiments according to the present disclosure, the nozzle body 1 can extend from another horizontal position of the fluid tank 2 into the fluid tank 2. Namely, the relative position between the nozzle body 1 and the fluid tank 2 is not limited in the present disclosure as long as the extension tubes 12 of the nozzle body 1 extend into the fluid tank 2 and the outlet port 121 of each extension tube 12 is located under the liquid level 21 to permit the oil phase fluid F1 to be driven into the water phase fluid F2.

Figure 11:
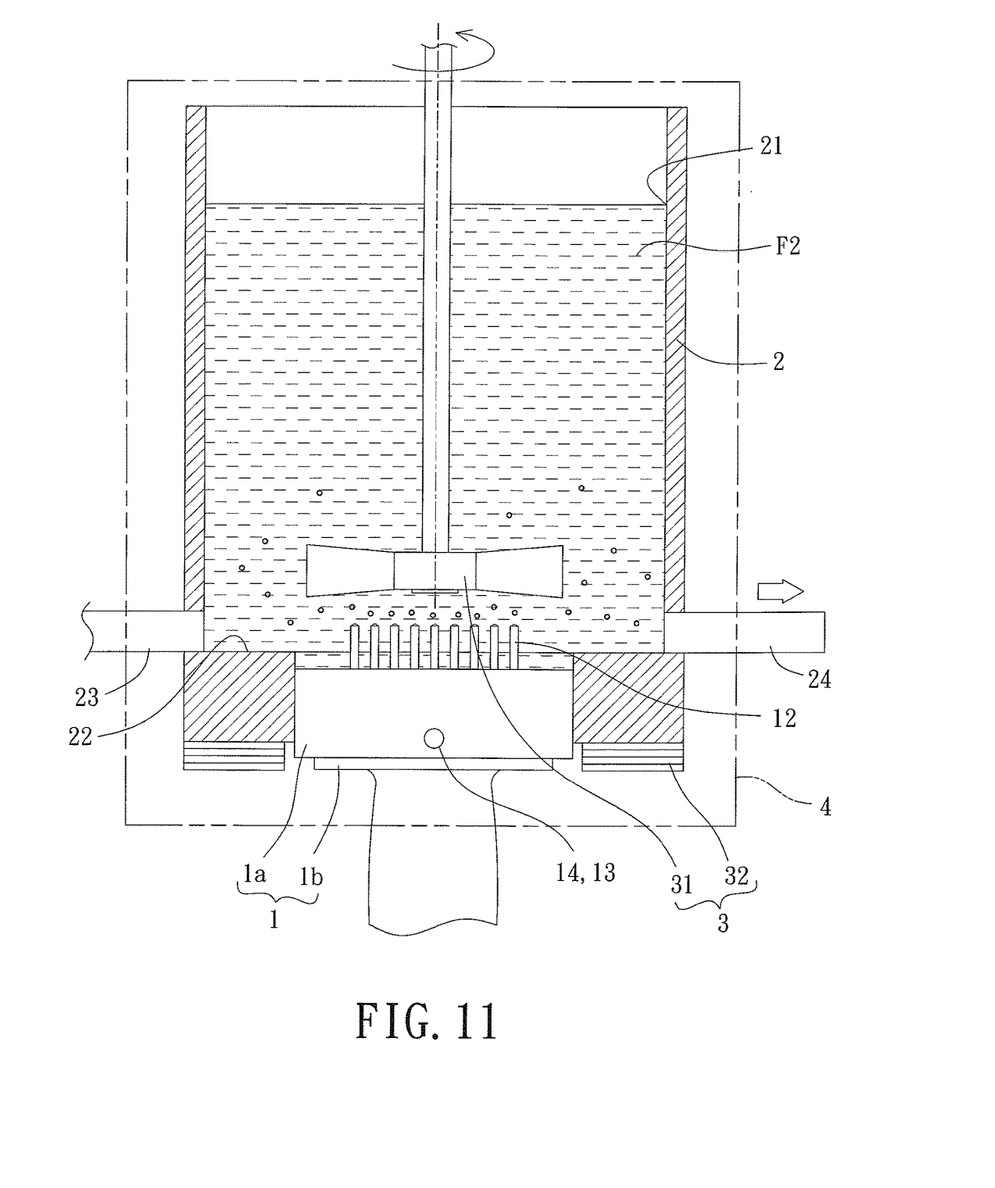
FIG. 11 is a cross sectional view of an apparatus for producing microparticles of another embodiment according to the present disclosure.

Furthermore, with reference to FIG. 4, in this embodiment, the temperature control system 4 can be a heating coil and is coupled to the outer wall of the fluid tank 2. Thus, the temperature control system 4 can heat the water phase fluid F2 via the outer wall of the fluid tank 2 to maintain the water phase fluid F2 at the predetermined temperature. Alternatively, as shown in FIG. 11, in some embodiments according to the present disclosure, the temperature control system 4 can be a thermostat box, and the fluid tank 2 can be mounted in the temperature control system 4. Thus, the temperature control system 4 can also maintain the water phase fluid F2 at the predetermined temperature.

In the method for producing microparticles of an embodiment according to the present disclosure, the temperature control system 4 is activated to maintain water phase fluid F2 at the predetermined temperature, such that the temperature of the water phase fluid F2 can assist in curing and shaping of the microdroplets while the oil phase fluid F1 are forming the microdroplets. Nevertheless, as mentioned above, the oil phase fluid F1 can be produced by adding a small amount of organic solvent into a polymer. Thus, in some cases, curing and shaping of the microdroplets formed by the oil phase fluid F1 may not be significantly related to the temperature of the water phase fluid F2. Consequently, the temperature control system 4 does not have to be activated in the method for producing microparticles in some embodiments according to the present disclosure.

Figure 12:
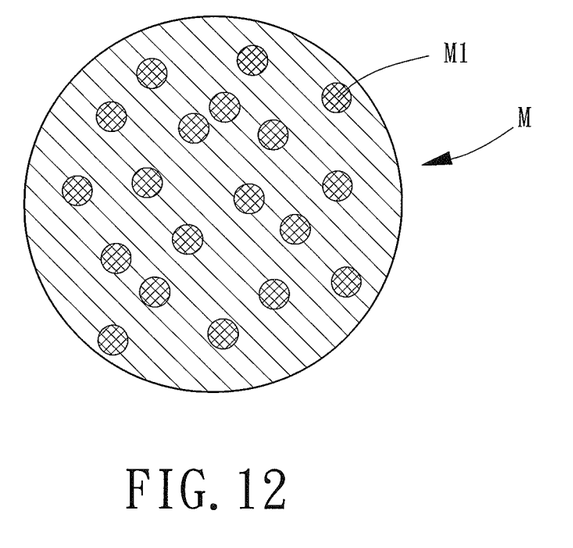
FIG. 12 is a diagrammatic view of a microparticle product produced by the apparatus for producing microparticles of an embodiment according to the present disclosure, with the microparticle product including a pharmaceutically active ingredient.
Figure 13:
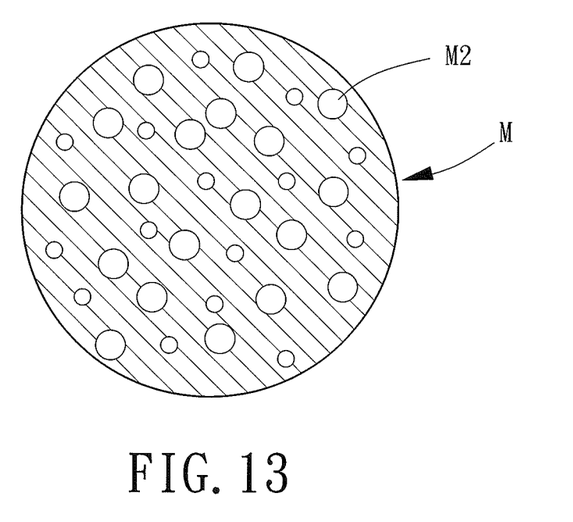
FIG. 13 is a diagrammatic view of a microparticle product produced by the apparatus for producing microparticles of an embodiment according to the present disclosure, with the microparticle product including micro gas bubbles.

Furthermore, the worker can change the composition of the oil phase fluid F1 to form the microparticle products M shown in FIG. 12. Specifically, as mentioned above, the oil phase fluid F1 can be a biodegradable polymer mixed with an active pharmaceutical ingredient M1 by emulsification, such that each microparticle product M contains the active pharmaceutical ingredient M1. Thus, when the microparticle products M are given to an organism, a slow releasing effect of the active pharmaceutical ingredient M1 is achieved by enveloping of the biodegradable polymer. Furthermore, by mixing the oil phase fluid F1 with a gas, microparticle products M shown in FIG. 13 can be obtained. Each microparticle product M contains a plurality of micro gas bubbles M2 to increase the drug releasing effect of the microparticle products M. Alternatively, the micro gas bubbles M2 in the form of voids in the microparticles provide a room for adherence of bacteria, increasing the number of adhered bacteria.

In view of the foregoing, the nozzle, method, and apparatus for producing microparticles according to the present disclosure use the nozzle body 1 to generate continuous oil phase fluids F1 and use the fluid shear device 3 to disturb the water phase fluid F2 in the fluid tank 2. The shear force or vibration of the water phase fluid F2 is used to interrupt the continuous oil phase fluids F1 to thereby form the semi-products of microdroplets and subsequently forming the microparticle products. The nozzle body 1 includes extension tubes 12 to prevent the oil phase fluid F1 from accumulating on each outlet port 121, such that the produced microparticle products M have more uniform diameters, reliably increasing the uniformity of microparticles.

Furthermore, since the apparatus and method for producing microparticles according to the present disclosure use the shear force or vibrations of the water phase fluid F2 to interrupt the continuous oil phase fluids F1, the rotational speed of the stirring device 31 can be adjusted to control the shear force of the water phase fluid F2. Alternatively, the frequency and amplitude of the supersonic wave generator 32 can be adjusted to control the vibrations of the water phase fluid F2. Accordingly, precise control of the diameters of the microparticle products M can be achieved. Furthermore, the present disclosure is suitable for producing microparticles from a high-concentration oil phase fluid F1, reliably increasing the control precision of the diameters of the microparticles while broadening the applications of the apparatus and method for producing microparticles.

Furthermore, the nozzle, apparatus, and method for producing microparticles according to the present disclosure make the oil phase fluid F1 continuously flow out of the nozzle body 1 at a faster speed, reducing the time for producing microparticles and reliably increasing the productivity of microparticles. Furthermore, the apparatus and method for producing microparticles use the stirring device 31 to drive the water phase fluid F2 to flow or use the supersonic wave generator 32 to vibrate the water phase fluid F2, such that the microdroplets formed by the oil phase fluid F1 are prevented from aggregating in the water phase fluid F2 to assure each microdroplet is enveloped and shaped by the water phase fluid F2, increasing the yield of the microparticles.

Thus since the present disclosure disclosed herein may be embodied in other specific forms without departing from the spirit or general characteristics thereof, some of which forms have been indicated, the embodiments described herein are to be considered in all respects illustrative and not restrictive. The scope of the present disclosure is to be indicated by the appended claims, rather than by the foregoing description, and all changes which come within the meaning and range of equivalency of the claims are intended to be embraced therein.

What is claimed is:

1. A nozzle for producing microparticles, comprising: a nozzle body including a fluid passageway therein, with a plurality of extension tubes communicated with an end of the fluid passageway, with each of the plurality of extension tubes including a distant end having an outlet port and located distant to the fluid passageway, and with the outlet ports of the plurality of extension tubes spaced from each other, wherein the distant end of each of the plurality of extension tubes having the outlet port includes a layer of hydrophobic material.

2. The nozzle for producing microparticles as claimed in claim 1, wherein the plurality of extension tubes is parallel to each other.

3. The nozzle for producing microparticles as claimed in claim 1, with the outlet port of each of the plurality of extension tubes having a diameter, and with each of the plurality of extension tubes including a tubular wall having a thickness smaller than the diameter.

4. The nozzle for producing microparticles as claimed in claim 1, with the outlet port of each of the plurality of extension tubes having a diameter, with two adjacent extension tubes having a minimum spacing therebetween, and with the minimum spacing being larger than the diameter.

5. The nozzle for producing microparticles as claimed in claim 1, wherein the distant end of each of the plurality of extension tubes having the outlet port is an inclined end.

6. An apparatus for producing microparticles, comprising:
a nozzle for producing microparticles, with the nozzle including a nozzle body having a fluid passageway therein, with a plurality of extension tubes communicated with an end of the fluid passageway, with each of the plurality of extension tubes including a distant end having an outlet port and located distant to the fluid passageway, and with the outlet ports of the plurality of extension tubes spaced from each other;
a fluid tank, with the plurality of extension tubes of the nozzle body extending into the fluid tank;
a fluid shear device mounted on the fluid tank; and
a temperature control system, with the fluid tank mounted in the temperature control system.

7. The apparatus for producing microparticles as claimed in claim 6, with the fluid tank receiving a water phase fluid, with the water phase fluid received in the fluid tank including a level defining a liquid level, and with the outlet port of each of the plurality of extension tubes located under the liquid level.

8. The apparatus for producing microparticles as claimed in claim 6, further comprising a collection tank, with an inlet pipe and an outlet pipe coupled to the fluid tank and extending through a wall of the fluid tank, and with the collection tank intercommunicated with the outlet pipe.

9. The apparatus for producing microparticles as claimed in claim 6, wherein the fluid shear device includes a stirring device mounted on the fluid tank.

10. The apparatus for producing microparticles as claimed in claim 6, wherein the fluid shear device includes a supersonic wave generator mounted to an outer wall of the fluid tank.

11. A method for producing microparticles using the apparatus as claimed in claim 6, with the method comprising:
filling a water phase fluid into the fluid tank, with the outlet port of each of the plurality of extension tubes located in the water phase fluid;
filling an oil phase fluid into the fluid passageway of the nozzle body, and making the oil phase fluid flow out of the nozzle body via the outlet ports of the plurality of extension tubes;
activating the fluid shear device to disturb the water phase fluid, and making the oil phase fluid flowing out of the outlet ports of the plurality of extension tubes form a plurality of semi-products of microparticles in the fluid tank;
collecting the semi-products of microparticles, with each of the plurality of semi-products of microparticles including an inner layer formed by the oil phase fluid and an outer layer formed by the water phase fluid; and
removing the outer layers of the plurality of semi-products of microparticles.

12. The method for producing microparticles as claimed in claim 11, wherein the oil phase fluid is produced by heating a polymer to a glass transition temperature.

13. The method for producing microparticles as claimed in claim 12, further comprising activating the temperature control system to maintain the water phase fluid at a predetermined temperature before the oil phase fluid enters the fluid passageway, and the predetermined temperature is equal to or lower than the glass transition temperature of the oil phase fluid.

14. The method for producing microparticles as claimed in claim 11, further comprising producing the oil phase fluid by adding an organic solvent into a polymer.

15. The method for producing microparticles as claimed in claim 11, wherein the oil phase fluid is a biodegradable polymer mixed with a pharmaceutically active ingredient.

16. The method for producing microparticles as claimed in claim 11, wherein the oil phase fluid is a biodegradable polymer mixed with a gas.

17. The method for producing microparticles as claimed in claim 11, wherein when the oil phase fluid enters the fluid passageway, pressurizing the fluid passageway to drive the oil phase fluid into the water phase fluid via each outlet port, thereby generating a continuous oil phase fluid.

18. The method for producing microparticles as claimed in claim 11, further comprising processing the plurality of semi-products of microparticles by drying or by washing by an aqueous solution to remove the outer layers of the plurality of semi-products.

* * * * *